(12) United States Patent
Puthli et al.

(10) Patent No.: US 6,534,090 B2
(45) Date of Patent: Mar. 18, 2003

(54) ORAL OSMOTIC CONTROLLED DRUG DELIVERY SYSTEM FOR A SPARINGLY SOLUBLE DRUG

(75) Inventors: Shivanand P. Puthli, Maharashtra (IN); Suma G. Menon, Maharashtra (IN); Jayant S. Karajgi, Maharashtra (IN); Nitin B. Dharmadhikari, Maharashtra (IN); Ratnesh H. Shrivastava, Maharashtra (IN); Pratibha S. Pilgaonkar, Maharashtra (IN)

(73) Assignee: Sun Pharmaceutical Advanced Research Centre Limited, Mumbai (IN)

( * ) Notice: Subject to any disclaimer, the term of this patent is extended or adjusted under 35 U.S.C. 154(b) by 0 days.

(21) Appl. No.: 09/891,848

(22) Filed: Jun. 26, 2001

(65) Prior Publication Data

US 2003/0008006 A1 Jan. 9, 2003

(30) Foreign Application Priority Data

Feb. 2, 2001 (IN) .................................. 119/MUM/2001

(51) Int. Cl.$^7$ .............................. A61K 9/24; A61K 9/14; A61K 9/16; A61K 9/50
(52) U.S. Cl. ........................ 424/473; 424/489; 424/469; 424/488; 424/493; 424/485; 424/486; 424/484
(58) Field of Search ................................ 424/473, 489, 424/469, 488, 493, 485, 486, 484

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,111,202 A | 9/1978 | Theeuwes | |
| 4,327,725 A | 5/1982 | Cortese et al. | |
| 4,553,973 A | 11/1985 | Edgren | |
| 4,685,918 A | 8/1987 | Amidon et al. | |
| 4,716,031 A | 12/1987 | Eckenhoff et al. | |
| 4,857,336 A | * 8/1989 | Khanna et al. | ............ 424/473 |
| 4,992,278 A | 2/1991 | Khanna et al. | |
| 5,122,543 A | 6/1992 | Khanna | |
| 5,284,662 A | 2/1994 | Koparkar et al. | |
| RE34,990 E | 7/1995 | Khanna et al. | |
| 5,874,418 A | * 2/1999 | Stella et al. | ............ 514/58 |

FOREIGN PATENT DOCUMENTS

GB   2150830   12/1983

OTHER PUBLICATIONS

Felix Theeuwes, "Elementary Osmotic Pump," J. of Pharm. Sciences, vol. 64, pp. 1987–1991 (Dec. 1975).
Luhtala, "Effects of Surfactants . . . ," Acta Pharm. Fenn., vol. 94 (1985) (Abstract No. 1726, Derwent 85–38113).

* cited by examiner

Primary Examiner—Thurman K. Page
Assistant Examiner—Blessing Fubara
(74) Attorney, Agent, or Firm—Proskauer Rose LLP

(57) ABSTRACT

The present invention is for an oral osmotic controlled drug delivery system for a sparingly soluble drug comprising:

a. a core comprising (i) finely particulate anhydrous carbamazepine (ii) a polymeric swelling agent consisting of one or more swellable hydrophilic polymers selected such that the polymeric swelling agent exhibits controlled swelling and the wall does not rupture or burst, (iii) a crystal habit modifier in whose presence, upon contact with an aqueous medium, the anhydrous carbamazepine being transformed into cuboidal or rod-shaped crystals of the dihydrate of carbamazepine, or mixtures thereof, and (iv) water-soluble compounds for inducing osmosis, b. a wall made of acylated cellulose which is impermeable to the components of the core, but permeable to water, and c. a passageway through the wall for releasing the components present in the core to the surrounding environment.

11 Claims, No Drawings

ORAL OSMOTIC CONTROLLED DRUG DELIVERY SYSTEM FOR A SPARINGLY SOLUBLE DRUG

The present invention relates to an oral osmotic controlled drug delivery system for a sparingly soluble drug.

BACKGROUND OF THE INVENTION

Carbamazepine, 5H-dibenz-[b,f]azepine-5-carboxamide, is used as an anti-convulsant and is available commercially in the form of tablets, syrups, chewable tablets and extended-release formulations. It is used in patients who do not respond satisfactorily to other forms of treatment. The drug appears to act by reducing polysynaptic responses and by blocking post-tetanic potentiation.

The therapeutic range of carbamazepine is about 4–12 $\mu$g/ml. Blood levels of carbamazepine below 4 $\mu$g/ml are ineffective in treating clinical disorders, while levels above 12 $\mu$g/ml are most likely to result in side-effects. The side-effects are seen to a greater extent in syrup formulations due to the presence of fine particles of the active ingredient, which dissolve rapidly leading to faster drug absorption and higher peak plasma levels. The tablet formulations are relatively free of this disadvantage.

The oral osmotic system (OROS®, Alza Corp.), described by F. Theeuwes in J. Pharm. Sci., Vol. 64, 12, 1987–1991 (1975), consists of a therapeutic system in the form of a coated and/or a laminated monocompartment system, comprising, a semi-permeable wall/coat covering a drug-containing core and a passageway through the wall for releasing the contents of the core. Water permeates from the surrounding body fluids through the semi-permeable wall/coat and the pressure that is built-up causes a solution or suspension of the drug in the core to be released from the passageway. When a suspension of the drug is released, the released drug crystals dissolve and the dissolved drug is available for absorption from the gastrointestinal fluids into the general circulation. Hereinafter, the term "release" is used while referring to release of a suspension of a drug from an osmotic system and the term "delivery" or "drug delivery" is used in reference to appearance of dissolved drug in dissolution fluids or gastrointestinal fluids.

The OROS® system is unsuitable for drugs like carbamazepine, which are sparingly soluble in water and thus the osmotic pressure generated by the drug on its own is too low to cause release of the drug formulation from the core at a constant rate. Incorporation of an osmotic agent other than the drug itself requires fabrication of a two-layered osmotic system, one layer containing the drug and a second layer containing the osmotic agent and a swelling agent. Osmotic influx of water causes the swelling of a swellable polymer in the core and expels the contents of the drug compartment through the orifice. As compared to single compartment systems, the manufacture of two-compartment systems is more complicated. Another problem is that anhydrous carbamazepine (amorphous or crystalline) gets converted to the dihydrate form in an aqueous environment. These dihydrate crystals are needle-shaped and grow to ca. 500 $\mu$m in size in the longitudinal direction. They affect the release of the drug formulation by blocking the passageway of the dosage form. Still another problem is that when known swelling agents such as polyvinylpyrrolidone, polyethylene oxide, polymethacrylate, etc are used in single compartment systems as the swellable polymer, the swelling pressure is so great that in contact with water the semi-permeable membrane bursts and the whole system disintegrates in the stomach after a short time.

The above mentioned drawbacks were overcome by a single compartment osmotic system disclosed in U.S. Pat. No. 4,857,336 ('336) reissued as RE 34990, assigned to Ciba-Geigy. The foregoing describe an oral therapeutic system comprising a core containing finely particulate anhydrous carbamazepine as a drug, hydroxypropyl methylcellulose (HPMC) as a protective colloid, a swellable hydrophilic polymer selected from the group consisting of poly-N-vinyl-2-pyrrolidone, polyvinyl alcohol, alkylene oxide homopolymers, methyl cellulose, ethyl cellulose, hydroxypropyl cellulose, hydroxyethyl cellulose, a copolymer of vinyl pyrrolidone and vinyl acetate, a mixture of a copolymer of vinyl pyrrolidone and vinyl acetate, and a homopolymer of ethylene oxide, and a water-soluble compound for inducing osmosis. HPMC herein works as a protective colloid such that it inhibits the ability of carbamazepine to change from the anhydrous form to any other form. Thus, in the presence of HPMC, the anhydrous carbamazepine crystals within the system remain in their original fine state without converting to large crystals of the dihydrate, which block the drug formulation releasing orifice. It is explained in lines 35–39 of column 4 of the '336 patent that the therapeutic system is therefore able to release carbamazepine microcrystals having a size of up to about 20 $\mu$m.

The oral osmotic dosage delivery form disclosed in U.S. Pat. No. 5,284,662 ('662) is an improvement over the system of the '336 patent and comprises a core comprising (i) carbamazepine, (ii) an effective amount of a crystal habit modifier for said carbamazepine selected from the group consisting of $C_{1-4}$alkyl cellulose, hydroxypropyl-$C_{1-4}$alkyl cellulose, sodium carboxymethyl cellulose, sodium carboxymethyl $C_{1-4}$alkyl cellulose, and gelatin, (iii) from about 2% to about 15% of the total core weight of a mixture of at least two different hydroxy-$C_1$–$C_4$-alkyl celluloses wherein the ratio of the higher viscosity to the lower viscosity hydroxy-$C_1$–$C_4$-alkyl cellulose is about 2:1, (iv) a $C_6$ sugar alcohol, (v) a mono-or di-saccharide, (vi) from 0 to an effective amount of a tabletting lubricant, and (vii) from 0 to an effective amount of a wetting agent, with the core surrounded by a semi-permeable wall with a hole that connects the core with the external environment. In comparison to the system of the '336 patent, the system disclosed in the '662 patent requires the presence of additional specific excipients, particularly a mono- or di-saccharide, more particularly a dextrate, and also requires the two different hydroxyalkyl celluloses to be present in a particular ratio of 2:1. These changes are said to result in a surprising and unexpectedly better product in that carbamazepine is released in a zero-order fashion over about 6 hours, whereas the system of the '336 patent having the two different hydroxyalkyl celluloses in a 1:1 ratio delivered only 33% of the carbamazepine in a zero-order fashion over a period of only about 4 hours. Although a broad group of cellulose-based polymers and gelatin are mentioned as crystal habit modifiers in the '662 patent, only hydroxypropyl methylcellulose is exemplified.

U.S. Pat. No. 4,992,278 ('278) discloses a peroral therapeutic system in tablet form for continuous and controlled administration of active ingredients that are sparingly soluble in water, and consists of (a) a casing made of a semi-permeable material, (b) a compressed core containing the active ingredient, a hydrophilic swelling polymer consisting of a mixture of a vinyl pyrrolidone/vinyl acetate copolymer with an ethylene oxide homopolymer, optionally a water soluble substance for inducing osmosis, and optionally other pharmaceutically acceptable adjuvants, and (c) a passage through the casing for transport of the components of the core to the surrounding aqueous body fluid. The patent teaches that when known swelling agents such as polyvinylpyrrolidone, polyethylene oxide, polymethacrylate and the like, are used in single compartment systems the swelling pressure is so great that in contact with water the semi-permeable membrane bursts and the whole system disintegrates in the stomach after a short time. The problem is said to be solved by the advantageous swelling polymer mixture of the '278 patent. However, the systems exemplified in the '278 patent use large quantities of polymer. It would be desirable to use swelling polymers having a high degree of swelling such that they are usable in small amounts and do not contribute to increase in size of the system. As such, a large tablet or capsule is difficult to swallow and is not often acceptable to the patient leading to non-compliance of prescribed dosage regimens.

U.S. Pat. No. 5,122,543 ('543) discloses an aqueous suspension in the form of syrup for the oral administration of carbamazepine. This suspension exhibits delayed drug delivery characteristics and improved stability, and comprises carbamazepine dihydrate crystals having cubic or cuboidal shape and a particle size of approximately 10 $\mu$m to approximately 200 $\mu$m, wherein said crystals are obtained by dispersing in water anhydrous carbamazepine and polyvinylpyrrolidone/vinyl acetate copolymer as crystal habit modifier. The patent teaches that the use of the larger cuboidal crystals of a size between 10 $\mu$m to 200 $\mu$m results in delayed drug delivery, in comparison to fine needle-shaped crystals of the dihydrate less than 10 $\mu$m in size. Syrups containing the finer needle-shaped crystals of the dihydrate make available a larger specific surface area for dissolution and absorption of carbamazepine. The greater side effects with syrups as opposed to tablets are attributed to the higher peak plasma levels of carbamazepine resulting from its rapid absorption.

OBJECTS OF THE INVENTION

It is the object of the present invention to provide an oral osmotic controlled drug delivery system, which provides the desired rate of delivery of carbamazepine preferably over a period of about 24 hours.

A further object of the present invention is to provide an oral osmotic controlled drug delivery system for carbamazepine which utilizes a novel polymeric swelling agent comprising one or more swellable hydrophilic polymers selected such that the polymeric swelling agent exhibits controlled swelling and the wall does not rupture or burst.

A still further object of the invention is to meet the above two objectives, particularly the latter objective, while using swelling polymers having a high degree of swelling such that they are usable in small amounts and do not contribute to an increase in size of the system. As such, a large tablet or capsule is difficult to swallow and is not often acceptable to the patient leading to non-compliance of prescribed dosage regimens.

A still further object of the invention is to provide a zero order rate of drug delivery for up to about 6 hours while meeting the above objectives.

We have found a novel osmotic controlled drug delivery system for oral administration of carbamazepine, which does not employ protective colloid of the type used in the prior art '336 and '662 patents, but employs a crystal habit modifier in whose presence upon contact with water, the anhydrous carbamazepine converts to cuboidal, or rod-shaped crystals, or mixtures thereof. In comparative experiments where anhydrous carbamazepine was suspended in water or aqueous solution of a crystal habit modifier, we found that whereas in the absence of a crystal habit modifier the anhydrous carbamazepine immediately transformed to long discrete needles of up to ca. 500 $\mu$m in length that clustered together forming larger agglomerates, and also whereas in the presence of hydroxypropyl methylcellulose the anhydrous carbamazepine microcrystals did not convert to the dihydrate crystals, in the presence of crystal habit modifiers in the oral osmotic controlled drug delivery system of the present invention the anhydrous carbamazepine converted to cuboidal, or rod-shaped crystals, or mixtures thereof, between about 10 $\mu$m and 600 $\mu$m in length. It is surprisingly found that in the present invention, these cuboidal and/or rod-shaped carbamazepine dihydrate crystals do not by themselves or by agglomeration or clustering cause blockage of the drug-releasing passageway when the drug formulation is squeezed out of the passageway due to the pressure created by the osmotic influx of water and swelling of the polymers. We have further found a novel mixture of swelling polymers such that upon contact with water the swelling pressure generated is not so great that the semi-permeable membrane bursts and at the same time the swelling polymers have a high degree of swelling such that they are usable in small amounts and do not contribute to an increase in size of the system. It was furthermore quite surprising that in spite of an inference that may be made from prior art U.S. Pat. No. 5,122,543 that crystal size is an important factor in carbamazepine dissolution, the oral osmotic controlled delivery system of the present invention, while exhibiting the above desirable characteristics and in spite of a change in crystal form and size, provided the desired rate and manner (zero order) of drug delivery.

SUMMARY OF THE INVENTION

The present invention provides an oral osmotic controlled drug delivery system for a sparingly soluble drug comprising:

a. a wall made of acylated cellulose which is impermeable to the components of a core, but permeable to water, b. a core comprising (i) finely particulate anhydrous carbamazepine (ii) a polymeric swelling agent consisting of one or more swellable hydrophilic polymers selected such that the polymeric swelling agent exhibits controlled swelling and the wall does not rupture or burst, (iii) a crystal habit modifier in whose presence, upon contact with an aqueous medium, the anhydrous carbamazepine being transformed into cuboidal, or rod-shaped crystals of the dihydrate of carbamazepine, or mixtures thereof, and (iv) water-soluble compounds for inducing osmosis, and c. a passageway through the wall for releasing the components present in the core to the surrounding environment.

DETAILED DESCRIPTION OF THE INVENTION

The present invention provides an oral osmotic controlled drug delivery system for a sparingly soluble drug. The system comprises of a core surrounded by a semi-permeable wall, which is permeable to water but impermeable to the contents of the core, e.g., the sparingly soluble drug, swellable hydrophilic polymers, osmotic agents and the like, and a passageway through the wall.

The active ingredient in the core is finely particulate anhydrous carbamazepine in amorphous or crystalline form.

The average particle size of the anhydrous carbamazepine is generally less than about 100 µm. In preferred embodiments, more than 90% of the particles are less than about 5 µm. The carbamazepine is present in an amount sufficient to deliver a therapeutically effective amount of the drug over the delivery period. Generally, the amount may be between 100 mg to 500 mg, more particularly, it is 100 mg, 200 mg, 300 mg or 400 mg.

The polymeric swelling agent in the core consists of one or more swellable hydrophilic polymers selected such that the polymeric swelling agent exhibits controlled swelling and the wall does not rupture or burst due to swelling. Suitable swellable hydrophilic polymers used to form the polymeric swelling agent of the present invention are selected from among polymers that can be of plant, animal, mineral or synthetic origin. Examples of such polymers include (A) cellulose derivatives such as hydroxy $C_{1-4}$ alkyl celluloses, hydroxy $C_{1-4}$ alkyl $C_{1-4}$ alkyl celluloses, carboxyalkyl celluloses and the like; (B) vinyl pyrrolidone polymers such as crosslinked polyvinylpyrrolidone or crospovidone; (C) copolymers of vinyl pyrrolidone and vinyl acetate; (D) gums of plant animal, mineral or synthetic origin such as (i) agar, alginates, carrageenan, furcellaran derived from marine plants, (ii) guar gum, gum arabic, gum tragacanth, karaya gum, locust bean gum, pectin derived from terrestrial plants, (iii) microbial polysaccharides such as dextran, gellan gum, rhamsan gum, welan gum, xanthan gum, and (iv) synthetic or semi-synthetic gums such as propylene glycol alginate, hydroxypropyl guar and modified starches like sodium starch glycolate. The swellable hydrophilic polymers are present in suitable amounts (e.g. about 1% to about 15% based on the weight of the core) such that the polymeric swelling agent exhibits controlled swelling and the wall does not rupture or burst, the desired rate of drug delivery is obtained and the polymeric swelling agent does not contribute significantly to increasing the size of the osmotic system. The polymeric swelling agent may comprise one or more of the above swellable hydrophilic polymers. Often, a mixture of two hydrophilic polymers provides the desired controlled swelling.

The preferred cellulose derivatives that may be used as swellable hydrophilic polymers in the polymeric swelling agent of the present invention include hydroxy $C_{1-4}$ alkyl celluloses such as hydroxymethyl cellulose, hydroxyethyl cellulose, hydroxypropyl cellulose and the like. For example, the polymeric swelling agent may be a mixture of two different types or two different grades of the hydroxy $C_{1-4}$ alkyl celluloses. In one more preferred embodiment of the present invention, the polymeric swelling agent is a mixture of two different grades of hydroxyethyl celluloses, still more preferably a mixture of hydroxyethyl cellulose 250H and hydroxyethyl cellulose 250L, wherein the designation "250" indicates the degree of substitution and "H" and "L" denote high and low viscosity, respectively. A preferred weight ratio of 250H to 250L is about 1:4 to about 4:1, more preferably about 1:2 to about 2:1. The hydroxy $C_{1-4}$ alkyl $C_{1-4}$ alkyl celluloses that may be used as swellable hydrophilic polymers include hydroxypropyl methylcellulose, hydroxypropyl ethylcellulose and the like. Carboxyalkyl celluloses like carboxymethyl cellulose and its alkali salts, and in more preferred embodiments of the present invention crosslinked carboxyalkyl celluloses like crosslinked carboxymethyl cellulose, commonly known as croscarmellose, and its alkali salts may also be used as the swellable hydrophilic polymers.

In another embodiment of the present invention, copolymers of vinyl pyrrolidone and vinyl acetate, in admixture with alkylene oxide homopolymers such as polypropylene oxide, preferably ethylene oxide homopolymers or in admixture with hydroxy $C_{1-4}$ alkyl celluloses, preferably hydroxyethyl cellulose, may be used as the polymeric swelling agent. The ethylene oxide homopolymers are commercially available as Polyox® (Union Carbide), having a degree of polymerization of ca. 2000 to 100,000, with the molecular weight ranging between 100,000 and 7,000,000 Daltons.

A still more preferred polymeric swelling agent that may be used in the present invention comprises a mixture of croscarmellose sodium and xanthan gum. Croscarmellose sodium is a crosslinked polymer of sodium carboxymethyl cellulose, also known as Ac-Di-Sol, and available commercially as Nymcel® ZSX, Pharmacel® XL, Primellose® or Solutab®. Xanthan gum is a high molecular weight microbial polysaccharide gum obtained by the aerobic fermentation of carbohydrates with Xanthomonas campestris. Xanthan gum is of several different grades that have varying particle sizes, and is available commercially as Rhodigel, Rhodigel EZ, Rhodigel 200, Keltrol T and Xanthan gum Type FF. A preferred embodiment of the present invention contains xanthan gum type FF, having a particle size such that 100% of the particles pass through ASTM 80#, and a minimum of 92% pass through ASTM 200#, where ASTM stands for American Society for Testing and Materials, and 80# indicates a sieve with 80 meshes, each of size 180 µm, present in a length of 2.54 cm in each transverse direction parallel to the wires, and 200# indicates a sieve with 200 meshes, each of size 75 µm, present in a length of 2.54 cm in each transverse direction parallel to the wires, the sieve being made of stainless steel, brass or other inert material. The croscarmellose sodium and xanthan gum are present in suitable amounts such that the polymeric swelling agent exhibits controlled swelling and the wall does not rupture or burst, the desired rate of drug delivery is obtained and the polymeric swelling agent does not contribute significantly to increasing the size of the osmotic system. Generally, the croscarmellose sodium may be present in an amount from about 1% to about 10%, preferably about 3% to about 4.5% by weight of the core; and the xanthan gum may be present in an amount from about 2% to about 5%, preferably about 3.5% to about 4% by weight of the core.

The core contains an effective amount of a crystal habit modifier, in whose presence, upon contact with an aqueous medium, anhydrous carbamazepine crystals are transformed to cuboidal, or rod-shaped crystals of the dihydrate of carbamazepine, or mixtures thereof, having a length of about 10 um to about 600 um. In this context, an "effective amount of crystal habit modifier" generally means about 0.1% to about 10% by weight based on the weight of the core. The crystal habit modifier may be any compound in whose presence carbamazepine crystals are transformed to cuboidal and/or rod-shaped crystals of the dihydrate of carbamazepine having a length on the order of about 10 um to about 600 um. However, it is generally a water-soluble polymer or a water swellable polymer or surfactant or mixture thereof, in whose presence carbamazepine crystals are transformed to cuboidal or rod-shaped crystals of the dihydrate of carbamazepine, or mixtures thereof Experiments conducted by us showed that vinylpyrrolidone polymers, polyethylene oxide polymers, polyethylene glycols, polyoxyethylene-polyoxypropylene glycol copolymers and-several surfactants worked successfully as crystal habit modifiers of the present invention. We found that within a range of pH typical of gastrointestinal fluid, in aqueous medium, the anhydrous carbamazepine was transformed to cuboidal and/ or rod-shaped crystals. Further specific examples of the crystal habit modifiers include polyvinylpyrrolidone having an average molecular weight of 1,000,000 Daltons, polyoxyethylene having an average molecular weight of 100,000 Daltons, polyethylene glycol 400, polyethylene glycol 8000, polyoxyethylene-polyoxypropylene having an average molecular weight of 7680 to 9510, polyoxyl 60 hydrogenated castor oil and long chain $C_{12}$–$C_{18}$ fatty acid glycerides. Particularly preferred crystal habit modifiers of the present invention include vinylpyrrolidone polymers, more particularly, vinylpyrrolidone/vinyl acetate copolymers.

Vinyl pyrrolidone polymers or polyvinylpyrrolidone (PVP), also referred to as Povidone, are synthetic polymers consisting essentially of linear 1-vinyl-2-pyrrolidinone groups, the degree of polymerization of which results in polymers of various molecular weights, the molecular weight ranging between 2500 and 3,000,000 Daltons. PVP is commercially available as Kollidon® (BASF); Plasdone® and Peristone® (General Aniline). PVP is classified into different grades on the basis of its viscosity in aqueous solution. Different grades of PVP available are PVP K-12, PVP K-15, PVP K-17, PVP K-25, PVP K-30, PVP K-60, PVP K-90 and PVP K-120. The K-value referred to in the above nomenclature is calculated from the viscosity of the PVP in aqueous solution, relative to that of water. The preferred vinyl pyrrolidone polymer for use as a crystal habit modifier is PVP K-90, having an approximate molecular weight of 1,000,000 Daltons. It is more preferably used in the present invention when the hydroxyalkyl celluloses are used as the swellable hydrophilic polymers.

The most preferred crystal habit modifier is a vinyl pyrrolidone/vinyl acetate copolymer having a monomer ratio of vinyl pyrrolidone to vinyl acetate of approximately 60:40 (% by weight) and a molecular weight of 60,000±15,000 Daltons. The preferred 60:40 copolymer is commercially available, for example, under the commercial name Kollidon® VA 64 (BASF). In preferred embodiment of the present invention, Kollidon® VA 64 is present in an amount ranging from about 0.1% to about 5%, more preferably about 2% to about 3% by weight of the core.

Water-soluble compounds suitable for inducing osmosis, i.e. osmotic agents or osmogents, include all pharmaceutically acceptable and pharmacologically inert water-soluble compounds referred to in the pharmacopias such as United States Pharmacopia, as well as in Remington: The Science and Practice of Pharmacy; edition 19; Mack Publishing Company, Easton, Pa. (1995). Pharmaceutically acceptable water-soluble salts of inorganic or organic acids, or non-ionic organic compounds with high water solubility, e.g., carbohydrates such as sugar, or amino acids, are generally preferred. The examples of agents used for inducing osmosis include inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like, and mixtures thereof. The amount of osmogents that may be used depends on the particular osmogent that is used and may range from about 1% to about 60% by weight of the core.

Further, additional pharmaceutical excipients may be present in the core. Examples of other additional excipients include those excipients which are used in tabletting, during the preparation of granules, e.g. binders, lubricants, glidants, dispersants, colorants and the like. Thus, it is possible to use conventional adjuvants like lactose, saccharose,sorbitol, mannitol, cellulose, microcrystalline cellulose, or magnesium stearate, in addition to those mentioned above. The lubricants are typically present in an amount ranging from about 0.5% to about 5% by weight of the core, preferably up to about 4%, more preferably up to about 3.5%, most preferably about 0.75% to about 2% by weight of the core. Preferred additional excipients are surface-active compounds as exemplified in U.S. Pat. No. 5,284,662. A preferred embodiment of the present invention includes sodium lauryl sulfate as the surfactant, in an amount ranging between about 0.1 % and about 5% by weight of the core, more preferably about 0.5% to about 0.75% by weight of the core.

The suitable materials that may be used in the present invention for forming the semi-permeable wall include polymeric microporous materials that are well known to those skilled in the art and have been described in prior arts, for example in U.S. Pat. No. 4,857,336 (U.S. Pat. No. RE 34990) and U.S. Pat. No. 5,284,662. The cellulose acetates are preferred materials for wall formation. A combination of cellulose acetates with different degrees of acetylation may be employed to form the semi-permeable wall. As the degree of acetylation of the cellulose acetate increases, the material becomes more impermeable to aqueous fluids. Hence, a suitable combination of the cellulose acetates should be used to impart impermeability to the wall. A hydroxy $C_1$–$C_4$ alkyl $C_1$–$C_4$ alkyl cellulose and a plasticiser may also be present as components of the semi-permeable wall.

A preferred combination for forming the wall is cellulose acetate, of two different types, with different degrees of acetylation, in an amount ranging from about 78% to about 82%, more preferably about 80% of the wall weight, a hydroxy $C_1$–$C_4$alkyl-$C_1$–$C_4$alkyl cellulose, preferably hydroxypropyl methylcellulose, present in an amount ranging between about 5% to about 10%, more preferably from about 7% to about 8% of the wall weight, a poly $C_2$–$C_4$ alkylene glycol, preferably polyethyleneglycol, more preferably, polyethyleneglycol 8000, in an amount ranging from about 10% to about 14%, more preferably from about 11.5% to about 12.5% of the wall weight, and a suitable solvent system to form the coating solution. A preferred embodiment of the invention contains cellulose acetate 320S and cellulose acetate 398-10 NF, with the weight ratio of 320 S: 398-10 NF being about 5:1 to about 8:1, more preferably about 6:1 to about 7:1, still more preferably about 6.2:1 to about 6.6:1.

The expression "a passageway through the wall for releasing the core components to the surrounding fluid" covers a suitable means for releasing the drug formulation from the therapeutic system. This passageway comprises orifices, bores or apertures and the like, through the semi-permeable wall prepared by various methods such as those mentioned in U.S. Pat. No. 3,916,899. The passageway acts as the connection between the drug-containing core and the aqueous fluid in the environment. The minimum diameter of this passageway should be greater than the maximum length of the cuboidal or rod-shaped dihydrate crystals of carbamazepine. However, the diameter of the orifice is restricted to a maximum value, in order to prevent movement of aqueous fluid into the drug-containing core by convection. The most suitable form of passageway is an orifice formed by mechanical or laser drilling of the semi-permeable wall.

The oral osmotic controlled drug delivery system of the invention is prepared by known methods, e.g. by mixing, granulation, compression, coating etc. The mixture can be dry granulated, wet granulated or can be directly compressed. In the wet granulation process, the crystal habit modifier and the surfactant are dissolved in the granulating solvent and this solution is added to the dry mixture of osmogents, swellable hydrophilic polymers, colorants and the like. Water is the preferred granulating agent. The drug is then added to this solution in a finely particulate form. The entire mix is then granulated and the granulates, after lubrication, are eventually compressed on a rotary compression machine using standard concave beveled edge punches. In case of dry granulation, the dry mixture of carbarnazepine, crystal habit modifier, osmogents, swellable hydrophilic polymers, colorants and the like is passed through a chilsonator to obtain slugs of the material, which are then passed through suitable sieves to obtain granules. These granules are lubricated with a suitable lubricant and compressed on a rotary compression machine. In case of direct compression, the components of the system are mixed thoroughly and directly compressed on a rotary compression machine. The compressed cores, obtained by any one of the above methods, are subjected to coating, molding, spraying, or immersion in a solution of a suitable material, to form the semi-permeable wall. An orifice is finally drilled into the semi-permeable wall using mechanical or laser drilling.

The examples that follow do not limit the scope of the invention and are presented as illustrations.

EXAMPLE 1

Tablet cores were prepared according to the formula given in Table 1 below.

TABLE 1

| No. | Ingredient | Quantity (mg) | Percent (%) by weight of the core |
|---|---|---|---|
| 1. | Carbamazepine | 200 | 36.37 |
| 2. | PVP K90 | 20 | 3.63 |
| 3. | Hydroxyethyl cellulose 250 L | 10 | 1.82 |
| 4. | Hydroxyethyl cellulose 250 H | 20 | 3.64 |
| 5. | Sodium chloride | 142.45 | 25.90 |
| 6. | Lactose monohydrate | 150 | 27.28 |
| 7. | Iron oxide red | 0.05 | 0.009 |
| 8. | Sodium lauryl sulfate | 2.5 | 0.45 |
| 9. | Magnesium stearate | 5 | 0.9 |
|  | Total | 550 | 100 |

The hydroxyethyl cellulose 250L, hydroxyethyl cellulose 250H, sodium chloride, lactose and iron oxide red were sifted and mixed to obtain a solid mixture. PVP K90 and sodium lauryl sulfate (SLS) were dissolved in water. The solid mixture, carbamazepine and a part of the aqueous solution of PVP K90 and SLS were mixed at a slow speed for 15 minutes. The rest of the aqueous solution of PVP K90 and SLS was then added till granulation end-point was reached. The granules thus obtained were dried at 60° C. to a moisture content of 2%. These granules were then passed through a #20 sieve and compressed to obtain the drug core. A layer of the coating solution, equivalent to 13–14% by weight of the drug-containing core, was then applied to the core in a perforated coating pan to form the semi-permeable wall, using dichloromethane and methanol as the solvents.

The composition of the coating solution is given in Table 2.

TABLE 2

| No. | Ingredient | Quantity (mg) | Percent by weight of the wall |
|---|---|---|---|
| 1. | Cellulose acetate 320 S | 53.25 | 71.72 |
| 2. | Cellulose acetate 398 10NF | 8.01 | 10.8 |
| 3. | Hydroxypropyl methyl cellulose, 15 cps | 5.72 | 7.71 |
| 4. | Polyethylene glycol 8000 | 7.25 | 9.77 |

The coated tablets were dried for 48 hrs. Finally, an orifice of suitable size was drilled into the coated tablet by laser-drilling the coat. The dissolution profile of the tablets was tested in a USP type I apparatus at 100 rpm in 900 ml of degassed water at 37±0.5° C. The drug delivery characteristics of the tablets are recorded in Table 3 below.

TABLE 3

| Time | % drug delivery (± S.D.) |
|---|---|
| 3 hours | 24 (± 4.92) |
| 6 hours | 57 (± 6.23) |
| 12 hours | 81 (± 5.31) |
| 24 hours | 91 (± 4.55) |

EXAMPLE 2

Tablet cores were prepared according to the formula given in Table 4 below.

TABLE 4

| No. | Ingredient | Quantity (mg) | Percent by weight of the core |
|---|---|---|---|
| 1. | Carbamazepine | 200 | 50.0 |
| 2. | Kollidon ® VA 64 | 10 | 2.5 |
| 3. | Ac-Di-Sol | 15 | 3.75 |
| 4. | Xanthan Gum | 15 | 3.75 |
| 5. | Sodium chloride | 76.22 | 19.06 |
| 6. | Lactose monohydrate | 76.22 | 19.06 |
| 7. | Iron oxide red | 0.05 | 0.013 |
| 8. | Sodium lauryl sulfate | 2.5 | 0.625 |
| 9. | Magnesium stearate | 5 | 1.25 |
|  | Total | 400 | 100 |

The process of preparation of the therapeutic system involves sifting of lactose, Ac-Di-Sol, xanthan gum, sodium chloride and iron oxide red, and mixing with carbamazepine and a solution of sodium lauryl sulfate and Kollidon VA 64® in water. The rest of the procedure is essentially similar to that given in Example 1. The composition of the coating solution used for coating the system is given in Table 5 below.

TABLE 5

| No. | Ingredient | Quantity (mg) | Percent by weight of the wall |
|---|---|---|---|
| 1. | Cellulose acetate 320 S | 54.53 | 69.92 |
| 2. | Cellulose acetate 398 10NF | 8.21 | 10.53 |
| 3. | Hydroxypropyl methylcellulose, 15 cps | 5.86 | 7.52 |
| 4. | Polyethylene glycol 8000 | 9.38 | 12.03 |

A layer of the coating solution, equivalent to 19–20% by weight of the core was applied using dichloromethane and methanol as the solvents. An orifice was drilled into the wall using a laser-drilling equipment, after drying the tablets.

The tablets so obtained were subjected to dissolution studies using the method given in Example 1. The drug delivery profile of the tablets is recorded in Table 6.

TABLE 6

| Time | % drug delivery (± S.D.) |
|---|---|
| 3 hours | 25 (± 2.65) |
| 6 hours | 51 (± 5.14) |
| 12 hours | 70 (± 3.32) |
| 24 hours | 79 (± 3.19) |

While the invention has been described by reference to specific embodiments, this was done for purposes of illustration only and should not be construed to limit the spirit or the scope of the invention.

We claim:

1. An oral osmotic controlled drug delivery system for a sparingly soluble drug comprising:
   a. a wall made of acylated cellulose,
   b. a core surrounded by the wall, the core comprising (i) finely particulate anhydrous carbamazepine, (ii) a mixture of xanthan gum and croscarmellose sodium as a polymeric swelling agent which exhibits controlled swelling and the wall does not rupture or burst, (iii) a crystal habit modifier in whose presence, upon contact with an aqueous medium, the anhydrous carbamazepine is transformed into cuboidal or rod-shaped crystals of the dihydrate of carbarnazepine, or mixtures thereof, and (iv) a water-soluble compound for inducing osmosis, the wall being impermeable to the components of the drug-containing core, but permeable to water, and
   c. a passageway through the wall for releasing the components present in the core to the surrounding environment.

2. An oral osmotic controlled drug delivery system as claimed in claim 1, wherein the xanthan gum has a particle size such that about 100% of the particles pass through a sieve of ASTM 80# and a minimum of about 92% of the particles pass through a sieve of ASTM 200#.

3. An oral osmotic controlled drug delivery system as claimed in claim 1, wherein the xanthan gum is present in amounts in the range from about 3.5% to about 4%, and the croscarmellose sodium is present in amounts in the range from about 3% to about 4.5% by weight of the core.

4. An oral osmotic controlled drug delivery system as claimed in claim 1, wherein the xanthan gum and the croscarmellose sodium are present in a 1:1 weight ratio.

5. An oral osmotic controlled drug delivery system as claimed in claim 1, wherein the crystal habit modifier is selected from a vinylpyrrolidone polymer, a vinylpyrrolidone/vinyl acetate polymer, a polyethylene oxide polymer, a polyethylene glycol, a polyoxyethylene-polyoxypropylene glycol copolymer, a polyoxyethylene castor oil derivative, a long chain $C_{12}$–$C_{18}$ fatty acid glyceride, and mixtures thereof.

6. An oral osmotic controlled drug delivery system as claimed in claim 1, wherein the crystal habit modifier comprises vinyl pyrrolidone/vinyl acetate copolymer having a monomer ratio of vinyl pyrrolidone to vinyl acetate of approximately 60:40 in % by weight.

7. An oral osmotic controlled drug delivery system as claimed in claim 1, wherein the crystal habit modifier comprises vinyl pyrrolidone/vinyl acetate copolymer in an amount from about 2% to about 3% by weight of the core.

8. An oral osmotic controlled drug delivery system as claimed in claim 1, wherein the crystal habit modifier comprises polyvinyl pyrrolidone having an approximate molecular weight of 1,000,000 Daltons.

9. An oral osmotic controlled drug delivery system of claim 1, wherein the acylated cellulose comprises one or more cellulose acetates, and the wall further comprises hydroxypropyl methylcellulose and polyethylene glycol 8000.

10. An oral osmotic controlled drug delivery system as claimed in claim 9, wherein one or more of the cellulose acetates comprises from about 78% to about 82% by weight of the wall, the hydroxypropyl methylcellulose comprises from about 5% to about 10% by weight of the wall and the polyethylene glycol 8000 comprises from about 10% to about 14% by weight of the wall.

11. An oral osmotic controlled drug delivery system as claimed in claim 1 wherein the cuboidal or rod-shaped crystals have a length of about 10 µm to about 600 µm.

* * * * *